(12) United States Patent
Slevin

(10) Patent No.: US 9,402,954 B1
(45) Date of Patent: Aug. 2, 2016

(54) MEDICAL INJECTOR

(71) Applicant: Richard S. Slevin, Los Altos Hills, CA (US)

(72) Inventor: Richard S. Slevin, Los Altos Hills, CA (US)

( * ) Notice: Subject to any disclaimer, the term of this patent is extended or adjusted under 35 U.S.C. 154(b) by 0 days.

(21) Appl. No.: 14/102,204

(22) Filed: Dec. 10, 2013

Related U.S. Application Data

(60) Provisional application No. 61/735,287, filed on Dec. 10, 2012.

(51) Int. Cl.
| | |
|---|---|
| *A61B 5/00* | (2006.01) |
| *A61M 5/00* | (2006.01) |
| *A61M 5/172* | (2006.01) |
| *A61M 5/20* | (2006.01) |
| *A61M 5/315* | (2006.01) |
| *A61B 5/145* | (2006.01) |
| *A61B 5/15* | (2006.01) |

(52) U.S. Cl.
CPC ............ *A61M 5/1723* (2013.01); *A61B 5/1411* (2013.01); *A61B 5/14532* (2013.01); *A61M 5/20* (2013.01); *A61M 5/31546* (2013.01); *A61M 2205/50* (2013.01); *A61M 2230/201* (2013.01)

(58) Field of Classification Search
CPC ............ A61B 5/14532; A61B 5/1411; A61B 5/4839; A61B 2562/0295; A61M 5/1723; A61M 2230/201; A61M 5/24
USPC ............ 604/66, 187, 71, 232; 600/365, 309, 600/316; 111/66, 187, 71, 232
See application file for complete search history.

(56) References Cited

U.S. PATENT DOCUMENTS

| | | | |
|---|---|---|---|
| 1,921,034 A | 8/1933 | Marche | |
| 4,392,859 A * | 7/1983 | Dent | 604/198 |
| 6,071,739 A * | 6/2000 | Vadgama et al. | 435/287.9 |
| 6,540,672 B1 * | 4/2003 | Simonsen et al. | 600/300 |
| 6,840,912 B2 | 1/2005 | Kloepfer et al. | |
| 7,901,364 B2 | 3/2011 | Kloepfer et al. | |
| 8,062,274 B2 | 11/2011 | Rasch-Menges et al. | |
| 2003/0105430 A1* | 6/2003 | Lavi et al. | 604/136 |
| 2004/0171983 A1* | 9/2004 | Sparks et al. | 604/65 |
| 2005/0101981 A1* | 5/2005 | Alden et al. | 606/181 |
| 2005/0177072 A1 | 8/2005 | Kloepfer et al. | |
| 2006/0173379 A1 | 8/2006 | Rasch-Menges et al. | |
| 2008/0200782 A1 | 8/2008 | Planman et al. | |
| 2008/0306444 A1 | 12/2008 | Brister et al. | |
| 2009/0192648 A1* | 7/2009 | Namineni et al. | 700/231 |
| 2010/0198107 A1 | 8/2010 | Groll et al. | |
| 2011/0282173 A1* | 11/2011 | Fonduca et al. | 600/365 |
| 2011/0313350 A1* | 12/2011 | Krulevitch et al. | 604/65 |
| 2012/0004637 A1 | 1/2012 | Krulevitch et al. | |
| 2012/0035446 A1 | 2/2012 | Hold et al. | |
| 2012/0046606 A1* | 2/2012 | Arefieg | 604/66 |
| 2012/0271197 A1 | 10/2012 | Castle et al. | |

\* cited by examiner

*Primary Examiner* — Kevin C Sirmons
*Assistant Examiner* — William Carpenter
(74) *Attorney, Agent, or Firm* — Patent Law Offices of Michael E. Woods; Michael E. Woods

(57) ABSTRACT

A medical device that automates protocol compliance by performing one or more of measuring relevant data, determining dosage, dispensing appropriate dosages, ordering supplies, updating protocol, contacting third-parties, logging events, and reporting data.

2 Claims, 2 Drawing Sheets

MEDICAL INJECTOR

CROSS REFERENCE TO RELATED APPLICATIONS

This application claims benefit of U.S. Patent Application No. 61/735,287 filed 10 Dec. 2012, the contents of which are hereby expressly incorporated by reference thereto in its entirety for all purposes.

FIELD OF THE INVENTION

The present invention relates generally to medical devices, and more specifically, but not exclusively, to a self-contained user system to measure a user parameter and to automatically dispense an appropriate dose responsive to the user parameter, and even more specifically to device that safely and automatically measures blood glucose level, determines an appropriate dosage of insulin, and injects the insulin while including wireless communication to update various status data to pharmacies, physicians, and caregivers.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Various medical conditions require monitoring of one or more user parameters, using measured parameters to establish a proper dose of a medicine, dispense the appropriate dose (sometimes with a syringe/hypodermic needle), and to maintain an adequate supply of non-expired medicine for anticipated future needs. These parameters, dosages, dispensation schedule, and supply information are ideally communicated to a third party.

Conventional solutions employ different modalities and equipment for these various aspects of treatment. For example, for a diabetic patient, there is a set of equipment used for determining blood glucose level. And then there is a different set of equipment for administering a dose of insulin. The patient typically must manually manage these supplies and the associated data, create any logs and distribute the information appropriately and timely. In some situations, a medical condition has associated life-threatening states that require prompt medical attention and/or emergency services. The user may not be able to obtain needed medical attention on their own which increases risks associated with the medical condition.

For many medical conditions, risks can be increased and prognosis adversely affected by not following the assigned protocol close enough. And the protocols can be complicated, making compliance more difficult. In some cases, protocols assigned to a user may not be optimum because of the challenges in following complex protocols. And protocols may be dependent upon several variables that also can make the protocol more complex. Add to this that the protocol may change over time, which can have an impact on the amount and type of supplies needed, high levels of compliance with the protocol can be difficult to achieve.

What is needed is a medical device that automates protocol compliance by performing one or more of measuring relevant data, determining dosage, dispensing appropriate dosages, ordering supplies, updating protocol, contacting third-parties, logging events, and reporting data.

BRIEF SUMMARY OF THE INVENTION

Disclosed is a medical device that automates protocol compliance by performing one or more of measuring relevant data, determining dosage, dispensing appropriate dosages, ordering supplies, updating protocol, contacting third-parties, logging events, and reporting data.

The following summary of the invention is provided to facilitate an understanding of some of technical features related to safe and automatic diabetic treatment, and is not intended to be a full description of the present invention. A full appreciation of the various aspects of the invention can be gained by taking the entire specification, claims, drawings, and abstract as a whole. The present invention is applicable to other medical conditions, other dispensation systems.

Some embodiments include an automated device that can in "one click" measure the blood glucose (BG) level of a diabetic patient, determine the dosage of insulin and inject the correct amount of insulin. The device also sends this information to a network communications device (e.g., the Internet or the Cloud), which in turn, is enabled to contact a pharmacy for refills, a physician and any other care giver or family/friend. The device is intended to be a 1-3 day use device having consumables/disposables which are changed periodically using cartridge systems. Aspects of these embodiments include: 1) auto-ordering and provisioning of the device from and to the cloud; 2) design of the device in a novel "pen" format and its industrial design and features; 3) specific individual features include: a) blood glucose (BG) mechanics (a cassette with automated lancing, movement of the test paper and determination of the BG level all in one step), b) an injection mechanism (a compound device that has several parts—first the device is pressure (or can be skin, capacitive) sensitive to open up a unique camera shutter like device, second the device automatically begins an injection cycle (the compound mechanism first moves the needle into the patient, then the stepper motor injects the correct amount of insulin, then retracts) and lifting the device away from the body auto closes the shutter, c) safety device (the injection has two measurement devices—the encoder that determines the amount of insulin and, an optical sensor that confirms the amount) and these two devices must match within prescribed tolerance or the injecting is stopped, and d) hygiene—for subcutaneous injections, the needle and the lance in the above BG test can both be reused as only IM and IV cannot be reused but these may have some blood or other contaminants on them, therefore the device includes a disposable alcohol "pill" to both ends, with the pill filled with an alcohol soaked material and the ends are sealed with a self-sealing rubberized bladder that both seals the alcohol from coming out, and also wipes the needle so there is no blood, contaminants on the needle as well as eliminating the "sting" if alcohol is present during injection.

Variations of this type of device can be used outside the Diabetes market to auto-inject and possibly do other diagnostic calculations and measured auto-injection, and reporting/monitoring.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Embodiments of the present invention provide a medical device that automates protocol compliance by performing one or more of measuring relevant data, determining dosage, dispensing appropriate dosages, ordering supplies, updating protocol, contacting third-parties, logging events, and reporting data. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Figures 1, 2:
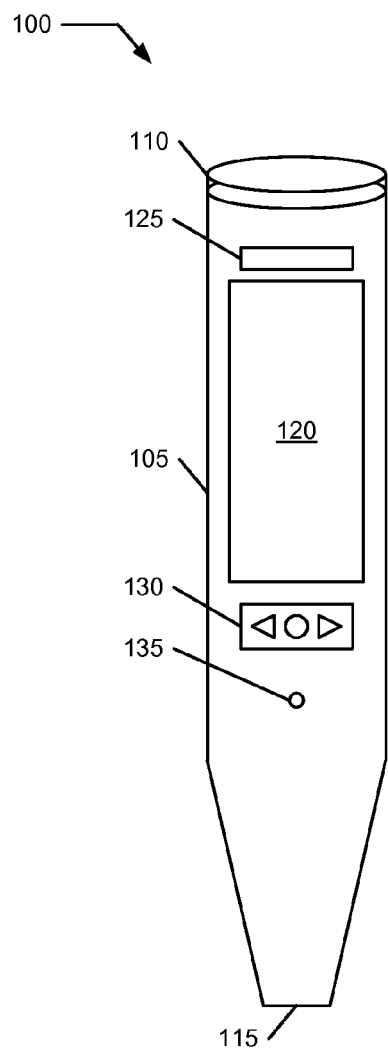
FIG. 1 illustrates a front view of a medical injector.
FIG. 2 illustrates a back view of the medical injector illustrated in FIG. 1.

FIG. 1 illustrates a front view of a medical injector 100. Injector 100 includes a housing 105 defining a sensor end 110 and a dispensing end 115. Housing 105 further supports a display 120 (e.g., LCD), a speaker 125, a user interface 130, and a microphone 135. Housing 105 defines a generally "pen" shaped format with sensor end 110 including data collection and dispensing end 115 proving an appropriate dose based upon the applicable protocol and data collected. In the aggregate, display 120, speaker 125, user interface 130, and microphone 135 are referred to as the I/O system. Some embodiments may have different/additional elements as part of the I/O system, such as a USB charge/communications plug.

Display 120 supports visual presentation of interface information for the user to configure and operate injector 100. Display 120 may support a cursor or other pointer element that may be repositioned. User interface 130 allows the user to position the cursor and to make selections, as necessary or desirable. For example, user interface 130 may include three buttons, one to move the cursor in a first direction, another to move the cursor in a second direction "opposite" to the first direction, and a third button to assert a selection/action signal. As further described herein, injector 100 includes wireless communication features that enable remote configuration and monitoring in addition to, or in lieu of, manual configuration using display 120 and user interface 130.

FIG. 2 illustrates a back view of medical injector 100. Housing 105 includes a latch 205 that selectively secures a back door that is removable to reveal an internal cavity supporting the features and components as described herein.

Figure 3:
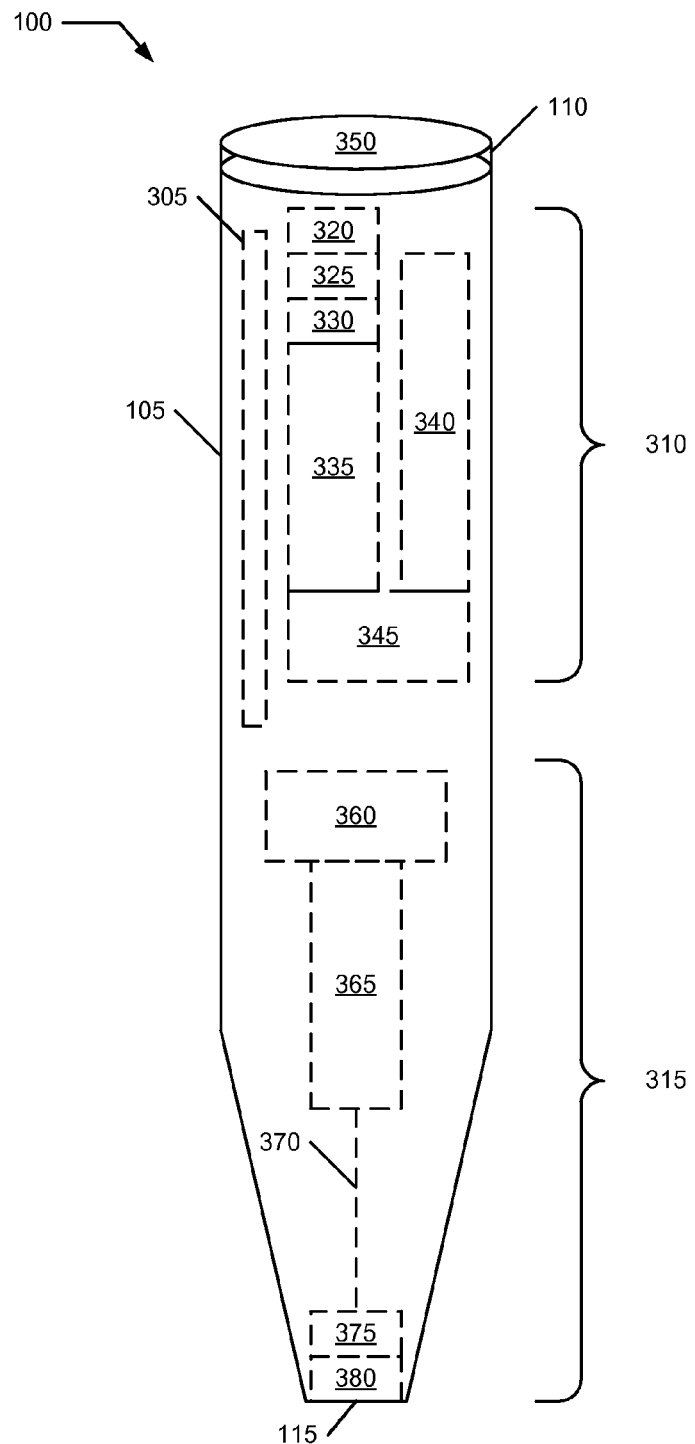
FIG. 3 illustrates a set of representative internal components for a medical injector of FIG. 1 configured for diabetes treatment.

FIG. 3 illustrates a set of representative internal components for medical injector 100 configured for diabetes treatment. Injector 100 includes three main subsystems: a controller 305, a data collection subsystem 310, and a dispensation subsystem 315. Data collection subsystem 310 and dispensation subsystem 315 are each preferably implemented as self-contained cartridge systems that provide consumables/disposables in easily replaced modules that are easily removed and replaced when the back door is removed.

Controller 305 includes a programmable storage computing system having a processor, a memory storing instructions executable by the processor, a rechargeable battery (e.g., lithium polymer), wireless communication device (e.g., a wireless transceiver using Bluetooth®, 802.11, cellular modem, Wi-Fi, and the like) and interface/control elements for the I/O system, data collection subsystem 310, and dispensation subsystem 315.

Data collection subsystem 310 includes a test sensor 320, a finger sensor 325 (e.g., capacitive or other finger touch/proximity-responsive sensor), an alcohol pill 330, a lance system 335, a test medium 340, and a supply of test media 345.

Sensor end 110 includes a lid 350 rotatably coupled to housing 105 that the user opens to access data collection subsystem 310. Rotating lid 350 and "clicking" finger sensor 325 initiates the automated data collection process of data collection subsystem 310. Some or all of the data control/processing needed or used by data collection subsystem 310 may be off-loaded to controller 305.

Dispensation subsystem 315 includes a motor 360 (e.g., motorized plunger injector with dosage encoder and the like), a syringe 365, a needle 370, and an alcohol pill 375. Motor 360 includes an encoder for precisely advancing a plunger coupled to syringe 365 storing the material (e.g., insulin) to be dispensed to the user through cannulated needle 370. Embodiments include a safety backup dosage sensor (e.g., infrared sensor or other sensing system) to cross-check a commanded dosage from dosage encoder with delivered dosage and to deactivate dosage delivery when there is a mismatch exceeding a predetermined threshold. Motor 360 advances needle 370 through alcohol pill 375 and out cover 380 before delivering the insulin. After delivery of the material, needle 370 is withdrawn into the cavity through cover 380 and alcohol pill 375. Alcohol pill 375 cleans and sterilizes the needle before and after use. Controller 305 controls, directly or indirectly, a total dose of insulin dispensed to the user.

Dispensing end 115 includes a cover 380 coupled to housing 105 that is pressure sensitive to open to allow needle 370 to extend through alcohol pill 375 and enter under the skin but not into the muscles or venous systems. Touching dispensing end 115 to an external portion of bare skin initiates the automated dosage delivery mechanism of dispensation subsystem 315. Some or all of the data control/processing needed or used by dispensation subsystem 315 may be off-loaded to controller 305.

In operation, in response to the initiation of the automated data collection process, injector 100 advances a lance of lance system 335 through alcohol pill 330 to clean and sterilize the lance before lancing the finger of the user that is at sensor end 110. Blood is collected on test medium 340 initiating a blood glucose (BG) test. Test sensor 320 evaluates the BG test and communicates the results to controller 305. After lancing, the lance is withdrawn through alcohol pill 330 and cleaned/sterilized prior to its next use.

Controller 305 evaluates the BG test and establishes a quantity of insulin to be injected. Information to effectuate the proper delivery of the determined dose is provided to dispensation subsystem 315. Controller monitors data from its operations and operations of the subsystems and creates logs of test results and dosages. When particular conditions are detected that meet pre-established boundary conditions, injector 100 contacts third-parties and provides them with appropriate information. These conditions include emergency conditions of BG, supply reordering, scheduled protocol updates, physician/caregiver compliance information, among other conditions.

The 1Clik™ medical injector is the next generation in diabetic care. It combines a blood glucose tester, insulin calculator, insulin injector, and secure wireless reporting to the cloud in one easy to use, fully automated device. With the 1Clik™ medical injector all daily supplies are carried within one device just slightly larger than a pen. Supplies are easily replenished: simply remove the back door and replace the Blood Glucose (BG) cassette and the insulin cartridge. When the user's BG test is at a dangerous level, the 1Clik™ medical injector can be set to automatically alert emergency services. The 1Clik™ medical injector can prompt you through the entire process or you can set it to silent mode. Either way, the LCD will show you clear, step by step instructions. 1Clik™ medical injector is also multi-lingual.

Here's how it works:

The 1Clik™ medical injector is truly easy to use. The 1Clik™ medical injector can be set to remind a user when they need to test by vibration and audio alarm, or send an e-mail/text message or other alert to you or a caregiver. The user can simply rotate the top until it "clicks" to start. That turns on the LCD screen, audio prompting, if enabled, and exposes the BG tester. The 1Clik™ medical injector will then say "place your finger on the tester". Note the LCD screen will also scroll all the verbal instructions.

To activate the tester, the user simply puts a finger on the tester. It is pressure sensitive and will not lance unless there is a finger on the tester. Once your finger is on the tester, the 1Clik™ medical injector will count down "5, 4, 3, 2, 1". After a few seconds, the BG tester will display your BG level followed by your insulin dosage. The 1Clik™ medical injector will then instruct you to place the injection tip on an injection site and hold. Once you do that, the pressure sensitive end cap will detect contact and activate the injection sequence. The 1Clik™ medical injector will count down "5, 4, 3, 2, 1" and perform the injection. It will also give you a summary, for example, "Injection completed; data was sent. Your next insulin injection is due at 2 PM today. You have 1 dose of insulin left. Your pharmacy has refilled your insulin prescription and it will be ready for pickup at 5:30 pm today. Thank you for using the 1Clik™ medical injector. Please rotate the cap to the off position; see you at 2 pm." That's all there is to it.

Supplies:

The BG cartridge contains a new lance, new test strips and a new alcohol pill that wipes the lance each time it is used, making sure to maintain sanitary conditions. The syringe can use standard syringes and needles, or you can elect to use the sealed syringe with the needle, in one convenient package, which comes with an integrated alcohol pill that wipes the needle each use. To replace these items is just one simple step, no lances or needles to fumble with: everything is in two simple cartridges.

Emergency Services:

The 1Click™ medical injector also has emergency features. If your BG is in the dangerous range, the 1Clik™ medical injector can call 911, your doctor, your friends, or family or other caregiver. Emergency call out can be cancelled within 15 seconds of the alarm by the user. Note: to use the call out feature, the user must have a communications system enabled, such as a Wi-Fi hot spot use the 1Clik Mobile™, or other communications system. Selected Features and Options: 1Clik™ comes in two formats; Wi-Fi and cell modem; Audio alarm can be programmed to use any ring tone or the default tones much like a cell phone; An ear bud can be used optionally for private audio prompting, and Ringtone or standard alarm programming.

Safety Considerations: the 1Clik™ medical injector is safe with backups in place BG Tester:

Finger Detection—The lancing process is initiated by a capacitance finger sensor buried under the test strip sensor area. The sensor detects the presence of a finger before any lancing is started. If the finger is pulled away during the process, the 1Clik™ medical injector will stop, and say and display that the lancing and BG test was aborted. 1Clik™ will tell you to repeat the process or cancel and shut down.

Retest—If the sample obtained from a test is insufficient, the 1Clik™ medical injector will ask you to repeat the test or cancel.

Hygiene—The lance cartridge has a small replaceable alcohol pill designed to clean the lance before and after use. It is in a self-sealing package so no alcohol leakage should occur. It also wipes the lance so no residual alcohol is on the lance that can sting the patient.

Injection:

Skin Detection—There is a sensor on the injection port that will sense when you have the injection end against the skin. The port will not open unless this is placed against the skin. Once placed against the skin the process will start. If the 1Clik™ medical injector is pulled away, the process is aborted. The 1Clik™ medical injector will give the user the option to try again or cancel.

Injection dosage—This is one of the most critical safety considerations. 1Clik™ has two measurement systems on board that must agree or the injection is aborted. One of these is an encoder built into the injection motor drive that feeds back the actual movement of the motor as it injects. This movement is directly related the injection volume. The secondary backup is an Infrared (IR) detector that visibly looks at the plunger location and verifies that the encoder reading is consistent with the IR reading. If these vary by more than 2%, the injection is immediately aborted and the 1Click™ medical injector tells the patient there is an internal error that must be fixed by the manufacturer. And, they must do a manual injection.

Dosage outside the range—If the BG analysis that the 1Clik™ medical injector takes results in a dosage that is more or less than the typical dosage for the patient by a settable percent (can be set by the physician and locked), the 1Clik™ medical injector will stop and give the user a warning. The user can override this if allowed (software settable) and continue. Or, if not allowed, the standard dosage will be used.

Wireless Cloud Reporting—In any event, all anomalies are immediately reported to the secure cloud interface and subsequently reported to the list connected with that account (doctor, family, friends, pharmacy, etc.).

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A medical injector for a user having a hand with a finger, comprising:

a pen-shaped housing defining a sensor end proximate the finger and a dispensing end opposite of said sensor end;

a data collection subsystem assembly, coupled within said housing proximate said sensor end and responsive to an assertion of a test signal, said data collection subsystem assembly including a first sterilizing system, a reusable lancing system, and a sample collection system, with said data collection subsystem configured to automatically execute a sterile lancing and blood sample collection procedure for the finger using said lancing system to engage the finger after sterilization of at least a portion of the reusable lancing system by said first sterilizing system to produce a sample of blood from the finger and to collect said sample using said sample collection system;

a dispensation subsystem assembly, coupled within said housing proximate said dispensing end and responsive to a dispensing signal, said dispensation subsystem assembly including a motor, a syringe including an injectable material, a reusable needle, and a second sterilizing system, with said dispensation subsystem assembly configured to subcutaneously inject an automatically determined quantity of said injectable material into the user through said reusable needle after automatic sterilization of said reusable needle within said housing; and a controller, coupled within said housing to said data collection subsystem assembly and to said dispensation subsystem assembly, said controller including a processor executing program instructions from a memory, for:

determining automatically a test result from said sample of blood;

determining said quantity of said injectable material responsive to said test result;

providing information effectuating an automatic delivery of said quantity of said injectable material to said dispensation subsystem assembly for an injection of said quantity of injectable into the user using said reusable needle;

wherein said assemblies are each independently replaceable modules;

wherein said injectable material is dispensed responsive to a movement of a plunger, wherein said motor is coupled to said plunger and includes an encoder configured to provide a feedback responsive to an injecting motion of said motor operating said plunger with said injecting motion directly related to an injection volume, wherein said dispensation subsystem assembly includes a first measurement system coupled to said encoder and a second measurement system coupled to said plunger measuring the plunger location related to the injection volume, wherein said controller compares said first measurement system to said second measurement system and is configured to abort and disable said automatic delivery of said quantity of said injectable material when an error is detected.

2. A medical injector for a user having a hand with a finger, comprising:

a pen-shaped housing defining a sensor end and a dispensing end opposite of said sensor end;

a data collection subsystem, coupled within said housing proximate said sensor end and responsive to an assertion of a test signal, said data collection subsystem including a first sterilizing system, a lancing system, and a sample collection system, with said data collection subsystem configured to automatically execute a sterile lancing and blood sample collection procedure for the finger using said lancing system to engage the finger after sterilization of at least a portion of the lancing system by said first sterilizing system to produce a sample of blood from the finger and to collect said sample using said sample collection system;

a dispensation subsystem, coupled within said housing proximate said dispensing end and responsive to a dispensing signal, said dispensation subsystem including a motor, a syringe including an injectable material, a needle, and a second sterilizing system, with said dispensation system configured to subcutaneously inject an automatically determined quantity of said injectable material into the user through said needle after automatic sterilization; and a controller, coupled within said housing to said data collection subsystem and to said dispensation subsystem, said controller including a processor executing program instructions from a memory, for:

determining automatically a test result from said sample of blood;

determining said quantity of said injectable responsive to said test result;

providing information effectuating automatic delivery of said quantity of said injectable to said dispensation subsystem for an injection of said quantity of injectable into the user;

wherein said injectable material is dispensed responsive to a movement of a plunger, wherein said motor is coupled to said plunger and includes an encoder configured to provide a feedback responsive to an injecting motion of said motor operating said plunger with said injecting motion directly related to an injection volume, wherein said dispensation subsystem includes a first measurement system coupled to said encoder and a second measurement system coupled to said plunger measuring the plunger location related to the injection volume, wherein said controller compares said first measurement system to said second measurement system and is configured to abort and disable said automatic delivery of said quantity of said injectable material when an error is detected.

* * * * *